(12) United States Patent
Ravin et al.

(10) Patent No.: US 7,091,035 B2
(45) Date of Patent: Aug. 15, 2006

(54) CELL CULTURING AND STORAGE SYSTEMS, DEVICES AND METHODS

(75) Inventors: Rea Ravin, Rockville, MD (US);
James V. Sullivan, Bowie, MD (US);
Ronald D. McKay, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 77 days.

(21) Appl. No.: 10/334,565

(22) Filed: Dec. 30, 2002

(65) Prior Publication Data

US 2004/0126876 A1   Jul. 1, 2004

(51) Int. Cl.
*C12M 3/00* (2006.01)

(52) U.S. Cl. .............. 435/288.3; 435/292.1; 435/293.1; 359/398

(58) Field of Classification Search ............ 435/288.3, 435/288.4, 288.7, 303.1, 304.1–304.4, 307.1, 435/809; 359/395, 398; 356/244; 422/102
See application file for complete search history.

(56) References Cited

U.S. PATENT DOCUMENTS

| | | | | |
|---|---|---|---|---|
| 2,090,914 A | * | 8/1937 | Porter | ......................... 359/398 |
| 2,940,360 A | * | 6/1960 | Carter, Jr. | .................... 359/398 |
| 3,591,461 A | * | 7/1971 | Bazil et al. | ............... 435/305.4 |
| 3,726,597 A | | 4/1973 | Dvorak et al. | ............... 356/244 |
| 4,629,862 A | * | 12/1986 | Kitagawa et al. | ............ 219/200 |
| 4,974,952 A | * | 12/1990 | Focht | ......................... 359/398 |
| 5,170,286 A | * | 12/1992 | Zimmerberg et al. | ....... 359/398 |
| 5,257,128 A | | 10/1993 | Diller et al. | ................. 359/395 |
| 5,449,620 A | * | 9/1995 | Khillan | .................... 435/288.3 |
| 5,459,069 A | * | 10/1995 | Palsson et al. | ........... 435/289.1 |
| 5,870,222 A | * | 2/1999 | Yamamoto et al. | ......... 359/368 |
| 6,008,010 A | * | 12/1999 | Greenberger et al. | ......... 435/41 |
| 2004/0003679 A1 | * | 1/2004 | Ide et al. | .................. 74/813 C |

FOREIGN PATENT DOCUMENTS

RU       2084893 C1  *  7/1997

* cited by examiner

*Primary Examiner*—William H. Beisner
(74) *Attorney, Agent, or Firm*—Peter F. Corless; Steven M. Jensen; Edwards Angell Palmer & Dodge LLP

(57) ABSTRACT

Featured is a long-term cell culture system being configured and arranged so as to be capable of monitoring the dynamic processes that occur during proliferation and differentiation of stem cells such as central nervous system (CNS) stem cells/embryonic stem cells. In particular aspects, the system allows monitoring of such dynamic processes continually and to focally manipulate the cells by focal application of growth factors such as BMP, CNTF and other growth factors. Preferred systems are capable of electrical recording from the cells.

20 Claims, 7 Drawing Sheets

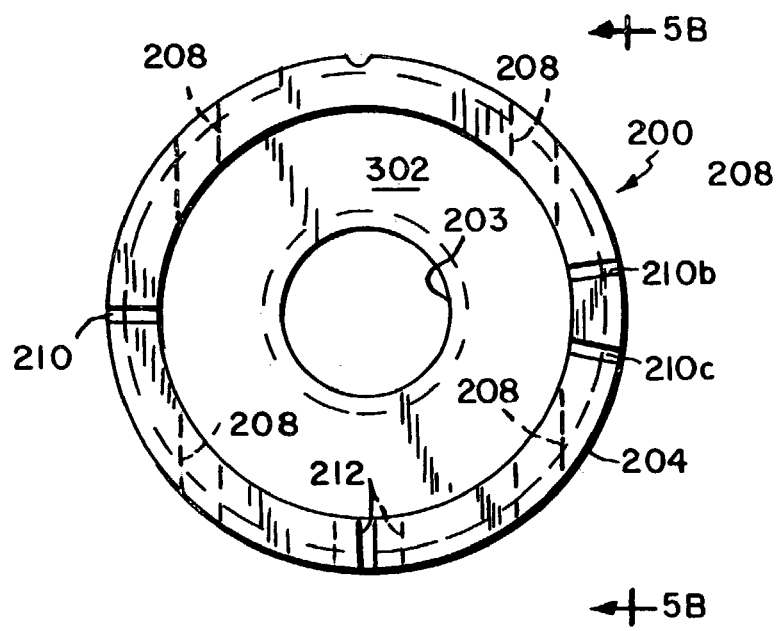
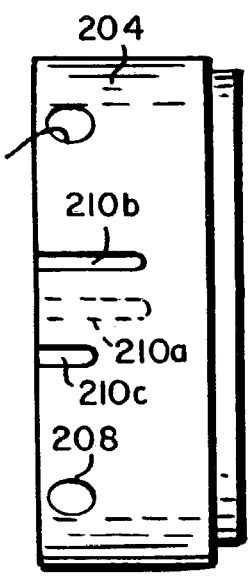
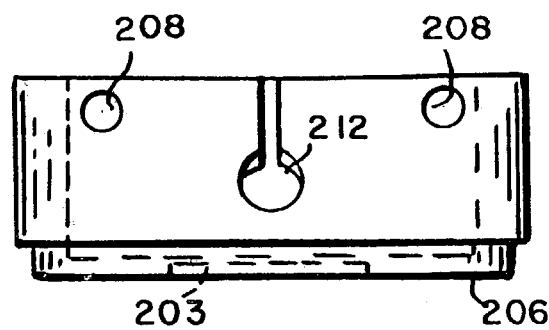
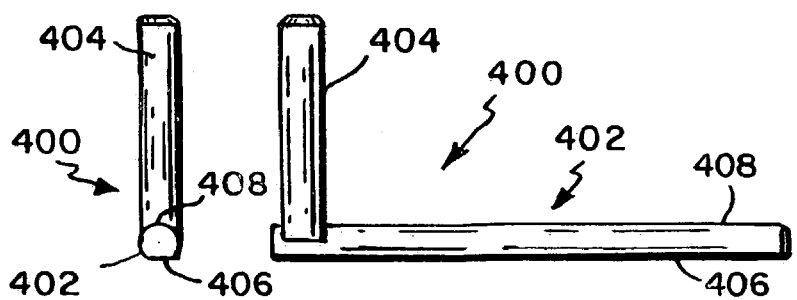
FIG. 4
FIG. 5B
FIG. 5A
FIG. 7　　FIG. 6

CELL CULTURING AND STORAGE SYSTEMS, DEVICES AND METHODS

BACKGROUND OF THE INVENTION

1. Field of the Invention

The present invention relates to systems that can monitor dynamic cell processes, including proliferation and differentiation of CNS stem cells/embryonic stem cells. Systems of the invention can allow monitoring of such dynamic processes continually and to manipulate the cells by focal application of growth factors. The present invention also relates to such systems that provide for the electrical recording from the cells as well as devices and components of such systems.

2. Background

Multicellular animals are derived from a clone of cells descended from a single original cell, the fertilized egg. Embryogenesis involves the division and differentiation of multipotential cells, each cell having the ability to develop into multiple cellular lineages. Phenotypically, the cells of such lineages can vary substantially, such as blood cells, muscle cells and neural cells, being specialized.

A wide spectrum of diseases may be treated based upon both the possession of a population of cells having multi-lineage potential and an understanding of the mechanisms that regulate embryonic cell development. For example, the capacity to generate a new population of hematopoietic cells is the basis of bone marrow transplantation, which is currently used as a treatment for a growing number of diseases including anemia, leukemia and breast cancer. In addition, transplantation of genetically altered multipotential cells has been considered as potential therapy for a variety of different diseases including AIDS.

One of the major barriers to both the treatment of diseases and the study of the process by which an undifferentiated embryonic cell becomes committed to a particular developmental pathway is the lack of access to populations of cells that are sufficiently multipotent to be able to develop into various lineages. In particular, much attention has been paid to the use of bone marrow stem cells as a source of multi-potential cells for therapy and experimental use. Bone marrow stem cells, however, have limited use because such populations of cells comprise a subpopulation of complex hematopoietic tissue and, therefore are rare. In addition, bone marrow stem cells have not been grown as a substantially homogeneous population in tissue culture.

Following fertilization, an egg divides over a period of days to form a blastocyst. A blastocyst includes a hollow ball of cells having an inner cell mass and a fluid-filled cavity, both encapsulated by a layer of trophoblast cells. The blastocyst then implants into the uterine wall and enters into the embryonic stage of development characterized by the formation of the placenta, the development of major internal organs and the appearance of major external body structure.

Cells from the inner cell mass of an embryo (i.e. blastocyst) can be used to derive a cell line capable of being maintained in tissue culture that is referred to as embryonic stem (ES) cells. The use of ES cells to obtain hematopoietic populations of differentiated cells has been suggested in Burkett et al., pp. 698–708. 1991, New Biologist, Vol. 3; Schmitt et al., pp. 728–740, 1991, Genes and Development, Vol. 5; Gutierrez-Ramos et al., pp. 9171–9175, 1992, Vol. 89; Keller et al., pp. 473–486, Mol. Cell. Biol., Vol 13; and Breier et al., pp. 521–532, 1992, Development, Vol. 114. The use of ES cells to obtain endothelial populations of differentiated cells has been suggested by Wang et al., pp. 303–316, 1992, Development, Vol 114.

Prior investigators, however, have failed to obtain populations of totipotent cells (i.e., cells that can develop into any lineage, discussed in detail below) and pluripotent cells (i.e., cells, that while unable to develop into all lineages of cells, are at least able to develop into all hematopoietic lineages, also discussed in detail below). A reason for this failure is that the ES cells were cultured under conditions in which the cells committed to a cellular lineage early in the tissue culture process. As a result, prior investigators failed to recognize a method for obtaining substantially homogeneous populations of totipotent or pluripotent embryonic cells that are useful for therapeutic or experimental use. In addition, prior investigators failed to recognize a method for inducing substantially homogeneous populations of totipotent or pluripotent cells to develop into preferred cell types.

It would be desirable to provide effective systems for culturing stem cells, including central nervous system (CNS) stem cells as well as components for such systems.

SUMMARY OF THE INVENTION

The present invention features new cell culture systems, apparatuses and devices that are capable of monitoring dynamic processes that occur during proliferation and differentiation of stem cells such as central nervous system (CNS) stem cells/embryonic stem cells. Also featured are methods related thereto.

Preferred systems of the invention are capable of allowing continual monitoring of such dynamic processes as well as manipulation of the cells by focal application of growth factors such as BMP, CNTF and the like. Preferably, systems of the invention also are capable of electrical recording from the cells. Such systems are particularly suited for the long-term culture of cells, particularly CNS stem cells, embryonic stem cells and the like.

Preferred cell culture systems of the invention can be suitably used in conjunction with any type of a wide variety of analysis equipment, materials or reagents, including equipment, materials and reagents used with standard microscope slides, such as for example, coverslips, slide washers, pipettors, or robotic systems. Additionally, the culture system of the invention can be analyzed using any type of instrument or device capable of analyzing or reading a standard microscope slide including for example, microscopes, scanners, readers, imagers or the like.

In other aspects of the invention, methods are provided for efficiently propagating undifferentiated germinal cells, e.g stem cells of the central nervous system (CNS) that is provided in long-term cell cultures. This provides the opportunity to monitor the growth, differentiation and proliferation under different conditions. For example, the conditions used can effectively turn the undifferentiated cells into mature cell types. These undifferentiated cells or "CNS stem cells" display the multipotential capacity to differentiate into all three major cell types of a mature brain neurons, astrocytes, and oligodendrocytes. Moreover, the same culture conditions enable isolation, expansion, and differentiation of equivalent multipotential cells from the adult brain.

In specific embodiments, a device of the invention comprises a cell culture system including an environmental chamber having an interior volume that is maintained under desired environment conditions; a microscopic viewing apparatus; a cell culture chamber having an interior volume in which cells are cultured, where the cell culture chamber is configured and arranged so as to allow light to pass through the chamber interior volume. Preferably the cell culture chamber and the microscopic viewing apparatus are arranged such that the viewing apparatus can view cells being cultured in the chamber interior volume.

In a preferred embodiment, the cell culture chamber of the cell culture system comprises a plurality of through apertures in communication with the interior volume that form one of an inlet port and an outlet port being used to control volume and flow of media to the chamber interior volume. In further embodiments, the plurality of through apertures of the cell culture system are configured and arranged so as to form two inlet ports and an outlet port, where one inlet port controls the volume and flow of a gas/gaseous mixture to the chamber interior volume and the other inlet port is for controlling the volume and flow of the media.

In another preferred embodiment the cell culture chamber further comprises a holder having a recess, and, an insert member, which is received in the holder recess. Preferably, the insert member is configured and arranged so as to comprise the chamber interior volume.

In another preferred embodiment, the cell culture chamber further comprises a mechanism for securing the insert member within the holder recess. Preferably, the insert member includes a body member having a through aperture extending along an axis thereof, and a plurality of cover members, a portion of each cover member allowing light to pass therethrough. Preferably, one of the plurality of cover members is positioned at one end of the body member through aperture so as to form a seal at said one end and another of the plurality of cover members is positioned at another end of the body member through aperture so as to form a seal at said another end thereby defining the chamber interior volume. Preferred cell culture devices or systems may include a mechanism for securing the insert member and the plurality of cover members within the holder recess.

In further preferred embodiment, the cell culture chamber further comprises a mechanism for one of continual monitoring the dynamic processes that occur during proliferation and differentiation of the cells being cultures, for manipulation of the cells such as for example by focal application of growth factors, and for electrical recording from the cells. In more particular embodiments, such a mechanism includes a ball joint assembly configured and arranged with an instrumentality, such as an electrode capillary for performing the foregoing functionalities.

Particularly preferred cell culture systems or devices of the invention are configured to enable viewing of the interior of the device by a user, particularly viewing of the cultured cells. Suitably, the device has one or more significantly translucent portions that enable viewing of the device interior, particularly to enable ambient light to enter the device and pass to the device interior.

Cell culture systems or devices of the invention preferably contain one or a plurality of through apertures in communication with the device interior volume. Suitably, the device contains a plurality of aperture where at least one aperture forms an inlet port and at least one aperture forms an outlet port that can be employed to control volume and flow of media to the chamber interior volume.

The cell culture device interior suitably may have a variety of configurations. In an especially preferred design, the interior chamber may comprise a holder element that has one or more recesses (e.g. a groove or lip) extending along or through at least a portion of an interior surface, and where an insert member can be nested within such a recess. The device may suitably comprise an apparatus to further secure the insert member within the recess.

Such an insert member may be configured to provide any of a number of functions. For instance, the insert member may be configured so that a portion(s) thereof is translucent (e.g. formed from a clear plastic) to enable viewing of the device interior as discussed above. Additionally, a removably nested component of the device, the insert can be readily withdrawn to facilitate cleaning of the device and the like.

Other aspects of the invention are disclosed infra.

BRIEF DESCRIPTION OF THE DRAWINGS

FIG. 4 is a top view of the stem cell chamber holder for the stem cell chamber of FIG. 2;

FIG. 5A is a side view of the stem cell chamber holder of FIG. 4;

FIG. 5B is another side view of the stem cell chamber holder when viewed from line 5B—5B of FIG. 4;

FIGS. 6–7 are a side and end view respectively of a locking member according to the present invention;

DETAILED DESCRIPTION OF THE INVENTION

According to one aspect of the present invention, there is featured a long-term cell culture system that is configured and arranged so as to be capable of monitoring the dynamic processes that occur during proliferation and differentiation of stem cells such as central nervous system (CNS) stem cells/embryonic stem cells. In particular, the system is configured and arranged so as to allow monitoring of these dynamic processes continually and to focally manipulate the cells by focal application of growth factors such as BMP, CNTF and other growth factors. Furthermore, the system also is configured and arranged so as to be capable of electrical recording from the cells. Such a as system is particularly suited for the long term culture of cells, particularly CNS stem cells, embryonic stem cells and the like.

The long term culture system of the present invention also can be suitably used in conjunction with any type of a wide variety of analysis equipment, materials or reagents, including equipment, materials and reagents used with standard microscope slides, such as for example, coverslips, slide washers, pipettors, or robotic systems. Additionally, culture system of the invention can be analyzed using any type of instrument or device capable of analyzing or reading a standard microscope slide including for example, microscopes, scanners, readers, imagers or the like.

According to other aspects of the present invention, there also is featured a method for efficiently propagating the undifferentiated germinal cells, i.e., stem cells of the central nervous system (CNS), that is provided in long term cell cultures. This provides the opportunity to monitor the growth, differentiation and proliferation under different conditions. For example, the conditions used can effectively turn the undifferentiated cells into mature cell types. These undifferentiated cells or "CNS stem cells" display the multipotential capacity to differentiate into all three major cell types of a mature brain—neurons, astrocytes, and oligodendrocytes. Moreover, the same culture conditions enable isolation, expansion, and differentiation of equivalent multipotential cells from the adult brain.

Figure 1:
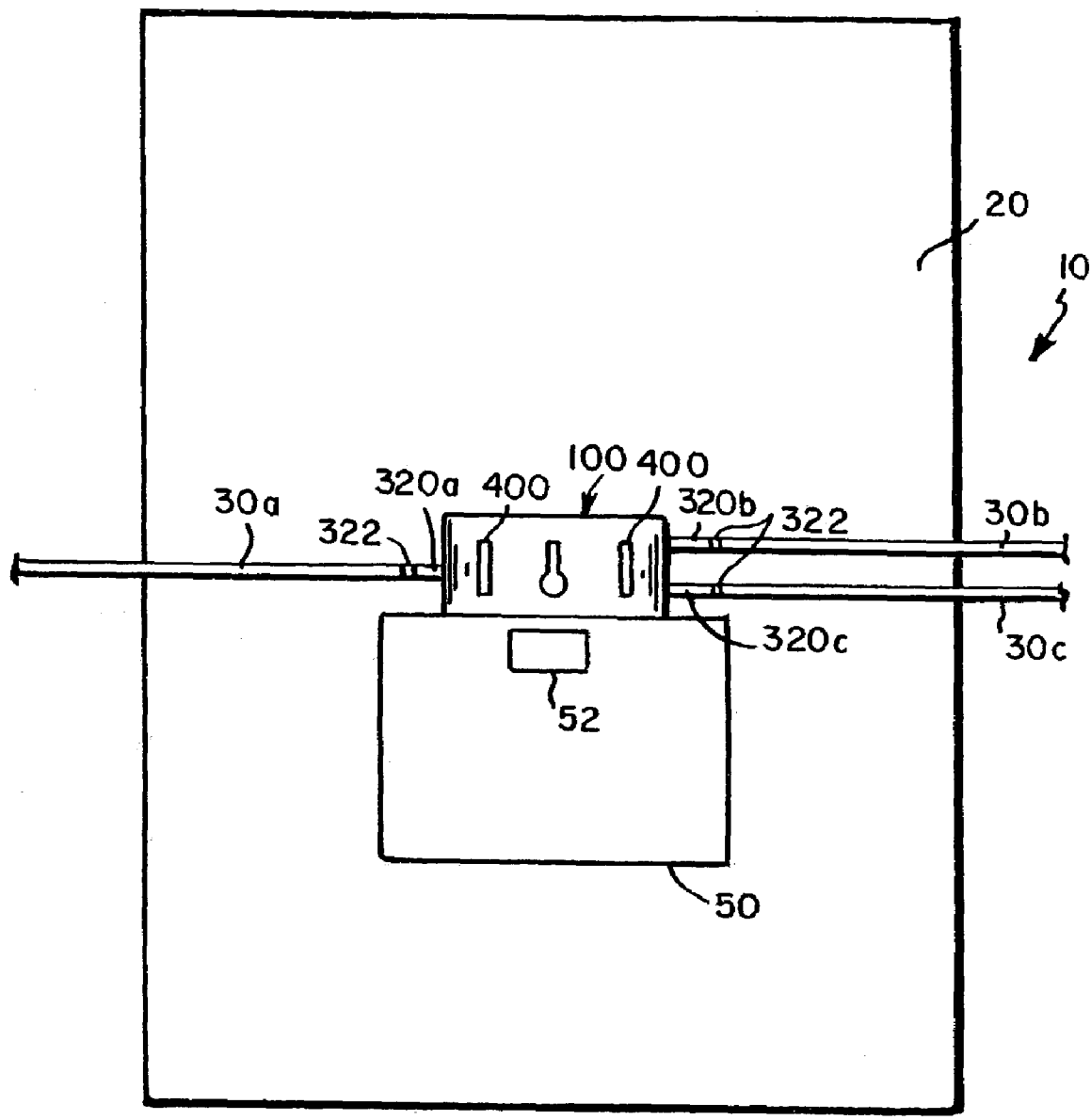
FIG. 1 is a schematic block diagram illustrating a cell culturing system according to an aspect of the present invention.

Referring now to the various drawing figures wherein like reference characters refer to like parts, there is shown in FIG. 1 a schematic block diagram of an illustrative example of a culturing system 10 used for the long term growth and monitoring of cells. It should be recognized that the illustrative example shown in FIG. 1 is not meant to limit or construe the invention in any way, but is provided for illustrative purposes. Such a culturing system 10 includes: an environmental chamber 20, a microscope stage 50, a stem cell chamber 100 and interconnecting tubing 30a–c that is fluidly interconnected to the stem cell chamber 100. The interconnecting tubing 30a–c is appropriately and separately interconnected to an external gas source (not shown) and to an external liquid source of nutrient or medium to promote or facilitate cell growth (not shown) that are used to create environmental conditions within the stem cell chamber that are conducive to growth. In a more particular embodiment, such external sources comprise syringe pumps or the like, that can meter the liquid or gas being inputted into the stem cell chamber 100 so as to be within a desired amount or range. In an exemplary embodiment, the external liquid source is capable of metering the flow of liquid so as to be in the range of from about 0.2 ml/hr. to about 0.5 ml/hr., more particularly about 0.5 ml/hr.

The environmental chamber 20 surrounds both the microscope stage 50 and the stem cell chamber 100. The environmental chamber 20 also is configured and arranged using any of a number of techniques known to those skilled in the art so as to selectively establish predetermined and desired environmental conditions within the environmental chamber. Such environmental conditions are established for purposes of warming the culture to temperatures conducive to growth and to minimize temperature variations that may not be conducive to growth. For example, by keeping the microscope stage 50 (e.g., the microscope thereof) continually in the same temperature as the culture, the microscope stage 50 does not become a heat sink, as it would if an unheated stage was introduced into the warmed environmental chamber 20, and so drift in focus also is prevented.

In an illustrative embodiment, the environmental chamber 20 is configured and arranged so as to maintain the stem cell chamber 100 and the microscope stage 50 at about 37° C. That is, in a preferred aspect, the microscope itself is contained within the environmental chamber.

The environmental chamber 20 also is configured an arranged using any of a number of techniques and materials known to those skilled in the art so as to form a structure that generally prevents transmission of light from the exterior to the interior volume of the environmental chamber. In this way, and as known to those skilled in the art, the light conditions within the interior of the environmental chamber 20 are controlled to those that are conducive to growth of the culture and, when viewing of the culture by the microscope stage 50 is desired, the lighting is controlled/adjusted so as to be optimal for such viewing. In more particular embodiments, the materials comprising the environmental chamber 20 include but are not limited to plastics and metals such as aluminum, and stainless steel.

The microscope stage 50 is any of a number of devices or apparatuses known to those skilled in the art that are used in high-resolution microscopy and that are appropriate for the intended use as well as for viewing the culture within the stem cell chamber 100 in the present invention. In more particular embodiments, the microscope stage 50 includes a light source to appropriately light the cells or culture within the stem cell chamber 100 for viewing.

Figure 2:
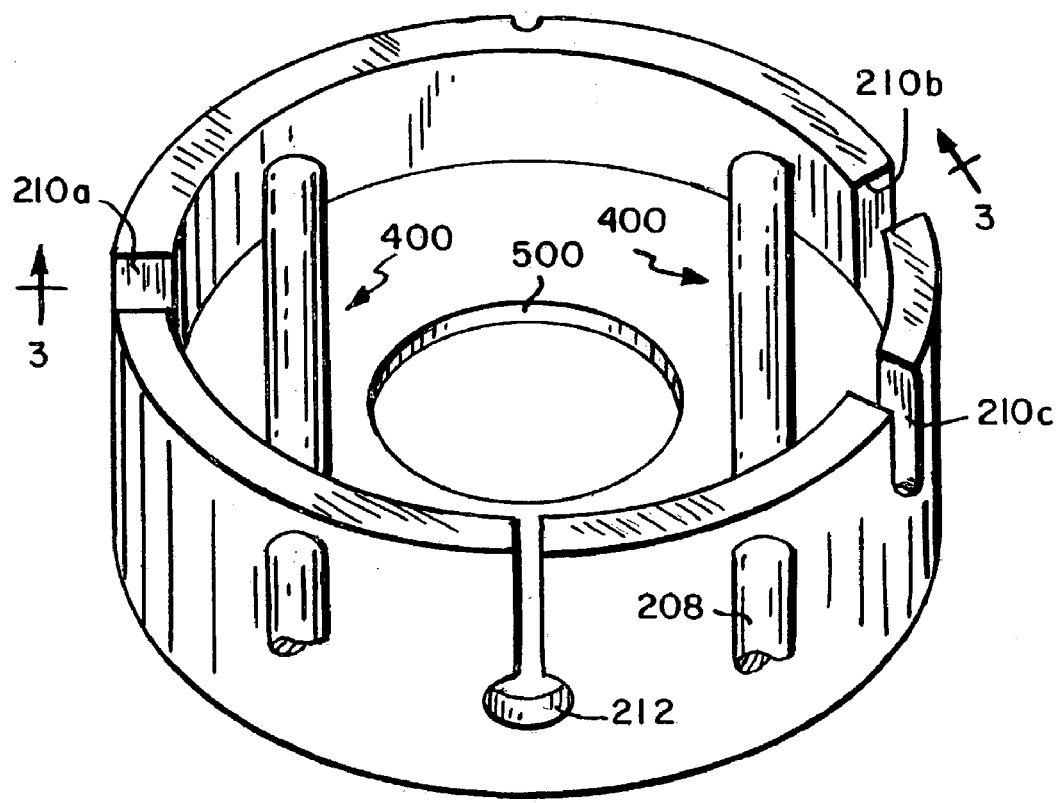
FIG. 2 is a perspective view of the stem cell chamber of FIG. 1 without the chamber insert tubing members for clarity.
Figure 3:
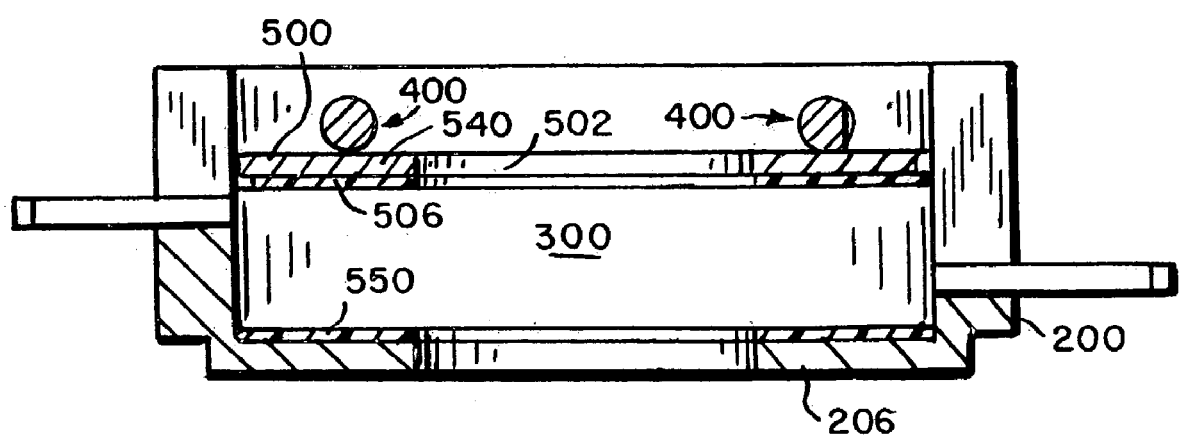
FIG. 3 is a cross-sectional view of the stem cell chamber taken along line 3—3 of FIG. 2.
Figure 8:
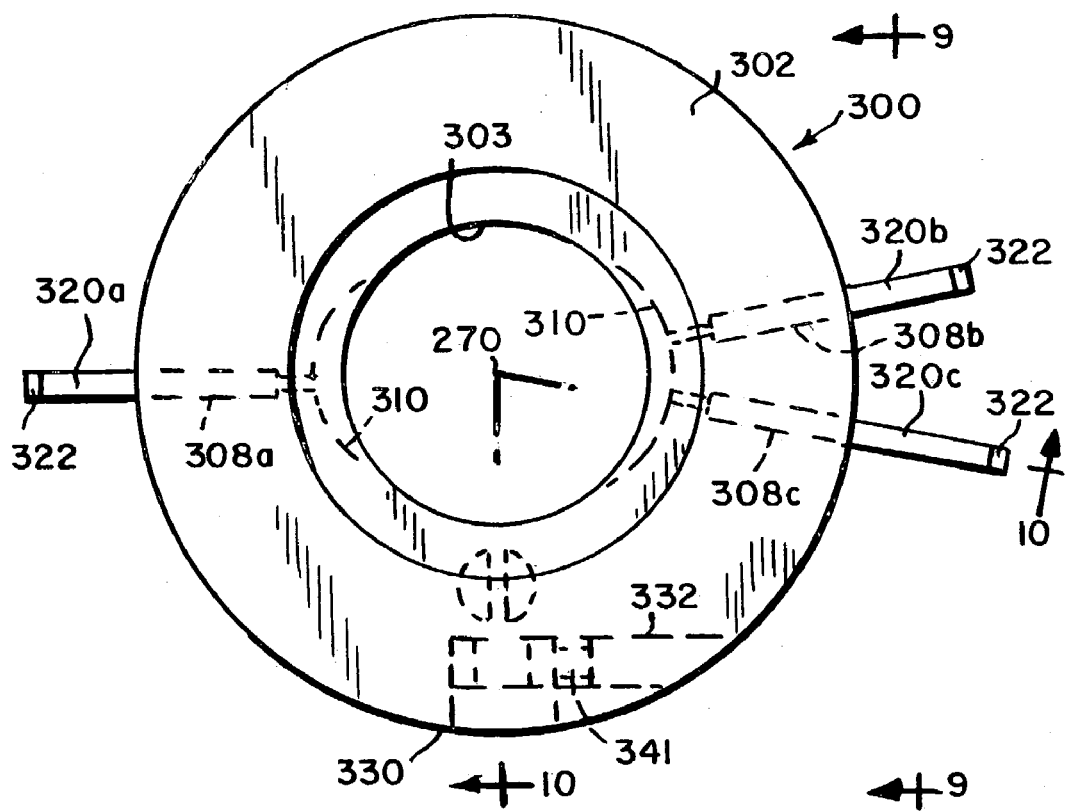
FIG. 8 is a top view of a chamber insert for the stem cell chamber of FIG. 2.
Figure 9:
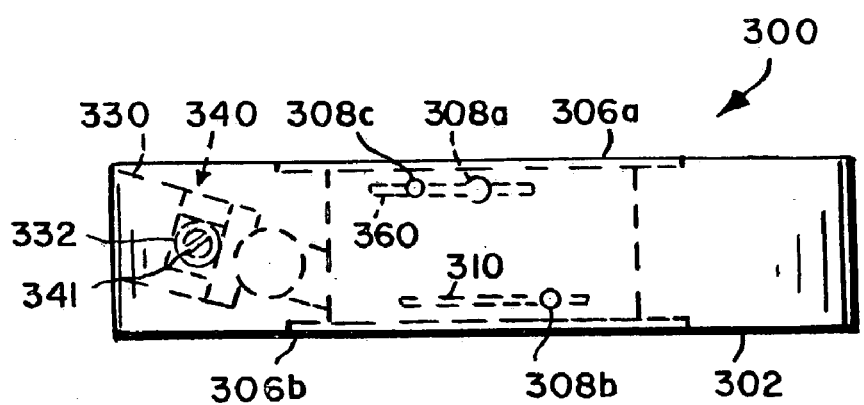
FIG. 9 is a side view of the chamber insert of FIG. 8 without the chamber insert tubing members for clarity.
Figure 10:
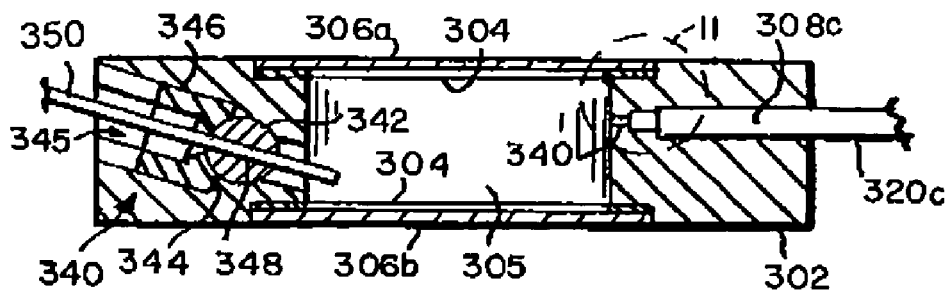
FIG. 10 is a cross-sectional view of the chamber insert taken along line 10—10 of FIG. 8.
Figure 11:
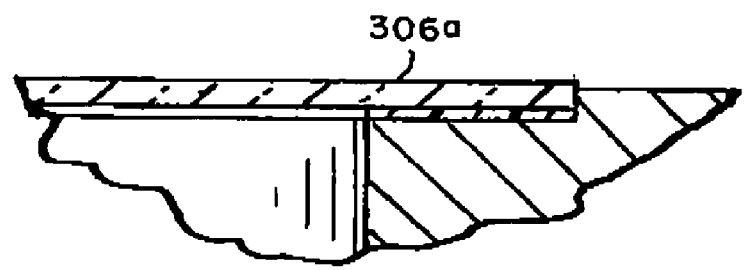
FIG. 11 is an expanded view of a portion of the cross-sectional view of FIG. 10.

Now referring also to FIGS. 2–3, there is shown a perspective and a cross section view of a stem cell chamber 100 according to the present invention, that includes a holder 200, a chamber insert 300, a plate member 500 and one or more locking members 400. In addition, reference also should be made to FIGS. 4–5 that illustrate various views of the holder 200, FIGS. 6–7 that illustrate various views of the locking members 400, FIGS. 8–10 that illustrate various views of the chamber insert 300, and FIGS. 11–12 that further illustrate features or components of the chamber insert.

The stem cell chamber 100 is a second environmental chamber that forms a mini gas-tight chamber that is placed over the microscope stage 50, more particularly in proximity to the microscope objective 52 of the microscope stage. Also, the stem cell chamber 100 is connected to a sealed circulating system, as is known to those skilled in the art, that maintains the gases within the cell chamber at a desired concentration and so as to maintain the liquid volume within the stem cell chamber at a desired level. In an exemplary embodiment, the gases in the stem cell chamber 100 are at a concentration of about 5% $CO_2$, 5% $O_2$. This configuration also allows for the growth of cells over the microscope stage 50 so as to allow imaging of the cells for long periods of time, such as for example, 2 weeks. Thus, the mini gas-tight chamber comprising the stem cell chamber 100 is a wet-dry chamber for addition of cell culture media and an appropriate gas mixture, which is determined by the type of cells to be cultured in/used with the system. For example, use of CNS stem cells are preferably cultured in an atmosphere comprised of 5% $CO_2$, 5% $O_2$ and 90% $N_2$.

The holder 200 is configured and arranged so as to include a recess 202 that forms a receptacle to receive therein the chamber insert 300 and plate member 500. The holder recess 202 is defined by sidewall(s) 204 that extend upwardly from a bottom 206 of the holder 200 and is generally dimensioned so the chamber insert 300 does not move appreciably in a radial direction when the insert is disposed within the recess.

In an illustrative embodiment, the holder 200 is generally cylindrical in shape, and the recess 202 also is arranged so that the recess also is generally cylindrical and so that it extends axially within the holder. This shall not be construed as limiting the shape of the holder 200, as the holder can be formed so as to have any geometric shape. Also, the recess 202 can be formed so as to complement the shape of the holder or be formed in another geometric shape that complements the shape of the chamber insert 300.

The plate member 500 is arranged within the holder recess 202 so to apply a pressure to the top most structure/surface of the seal chamber insert 300 when the lock member(s) is secured and positioned in the locked position. In more particular embodiments, the plate member 500 includes a pressure plate 504 to which is attached a compression ring 506. In more specific embodiments, the plate member 500 is configured with a through aperture 502 that is centrally positioned so as to allow light to pass through to the stem cell chamber insert 300 and the central area 305 therein.

In exemplary embodiments, the pressure plate 504 is made from any of a number of materials known in the art appropriate for the intended use, and more particularly materials that are capable of being sterilized using any of a number of techniques known to those skilled in the art, including sterilization by chemical, gas, radiation and heat (e.g., steam such as a steam autoclave). Such materials also are preferably inert materials that do not corrode, including but not limited to stainless steel, aluminum, chrome and the like. Also, in a further exemplary embodiment, the compression ring 506 comprises a silicon rubber disc bonded or otherwise securely attached to the pressure plate using any of a number of techniques known to those skilled in the art.

A bottom surface 212 of the recess 202 forms a shelf upon which at least a portion of a bottom surface of the chamber insert 300 rests against when the chamber insert is disposed within the recess. In more particular embodiments, the recess bottom surface 201 includes a through aperture 203 through which light can pass to the chamber insert 300. In addition, the holder bottom 306 (e.g., bottom thickness) is preferably dimensioned so that the specimen, culture, cell(s), etc, within the cell chamber 100 to be imaged or viewed are positioned in close proximity to the microscope objective 52 of the microscope stage 50 (FIG. 1) so as to provide for high resolution microscopy.

In further embodiments, the stem cell chamber 100 further comprises a ring member 550 that is disposed between the bottom surface of the chamber insert 300 and the bottom surface 201 of the holder recess 202. The ring member 550 is more particularly configured so as to compensate for possible variations and/or imperfections in the bottom surface of the chamber insert 300 and in the recess bottom surface 201, such that a sealing force is applied lower to the chamber insert 300, more particularly to the lower cover glass element 306*b* and its corresponding gasket 304. In further embodiments, the ring member 550 is made a resilient material, such as for example reinforced silicon rubber. The ring member 550 also is configured with a centrally located through aperture sufficiently sized such that the central area 305 of the chamber insert 300 can be viewed via the through aperture 203 in the recess bottom surface 201.

The holder 200 also is configured so as to include a plurality of sidewall slots 210*a–c* for receiving therein the tubular members or the insert tubing members 320*a–c* that are fluidly coupled to the chamber insert 300 as hereinafter described. In a particular embodiment, two of the sidewall slots 210*b,c* are arranged so that they lie in different planes such as that illustrated in FIG. 9, however, this is not particularly limiting as it is also contemplated that the sidewall slots be arranged so as to lie in the same plane. In particular embodiments, each of the sidewall slots 210*a–c* is configured so as to extend downwardly from a top surface of the holder 200. More particularly, each of the sidewall slots 210*a–c* extends downwardly a predetermined distance; the predetermined distance being set so the insert tubing members 320*a–c* passes through the respective sidewall slot and so the chamber insert 300 is essentially resting on the recess bottom surface 201 or the ring member 550. In further embodiments, the lower portion of each of the sidewall slots 210*a–c* is configured so as to complement the shape of the insert tubing members 320*a–c*; more particularly the lower portion suitably has a curved configuration, although other configurations also will be suitable such as square and other openings that will provide passage of tubes.

In addition, the holder 200 is further configured with a slotted through aperture 212, that passes through the holder sidewall 204. The slotted through aperture 212 includes a circular portion, circular in cross section, and a slot that extends generally radially outward from the circular portion. In more particular embodiments, the slot extends from the circular portion to the top surface of the holder 200. In more specific embodiments, the circular portion is formed at an angle with respect to normal of the sidewall, more specifically at angle such that the circular portion is angled downwards towards the recess bottom surface 201. Reference also shall be made to the following discussion regarding the ball joint assembly 340 of the chamber insert 300 as to further details for the slotted through aperture.

The holder 200 further includes at least one pair, more particularly one pair of locking member through apertures 208, where the each of the through apertures of each pair are disposed opposite to each other in the sidewall(s) 204 so the long axis of each through aperture are coincident or aligned with each other.

As shown in FIGS. 6–7, each of the locking members 400 comprises a long portion 402 and a handle portion 404 that extends generally perpendicular to a long axis of the long portion. As more clearly shown in FIG. 2, the long portion 402 of each locking member 400 is successively received in the locking member through aperture 208 of each pair of through apertures and so a segment of the long portion 402 of each locking member extends between the sidewall(s) within the recess and also is disposed over the plate member 500. In this way, the long portion 402 of each locking member in combination with the locking member through apertures 208, exert a force on the top surface of the chamber insert 300 as herein described thereby also generating a sealing force for the chamber insert. As also described hereinafter, the ability to easily lock and unlock allows the specimen, cells etc, disposed in the chamber insert 300 as well as replaceable elements thereof to be easily exchanged with other specimen, cells etc. and replaceable chamber insert elements.

In particular embodiments, the long portion 402 of each locking member 400 is configured so as to be generally circular in cross-section and more specifically having an arcuate or circular portion 408 and a portion that is configured so as to be substantially flat, a flat portion 406. The flat portion 406 and the circular portion 408 are generally configured and arranged such that a force is not exerted against the plate member 500 when the locking member 400 is disposed within the locking through apertures 208 and when the flat portion 406 is positioned opposite the plate member. Correspondingly, when the locking member 400 is rotated within the locking member through apertures 208, the circular portion 408 is rotated so as to be in contact/ mechanical engagement with the plate member 500 thereby applying a force to the plate member and thus also applying a sealing force to the chamber insert 300. In this way, by rotating the locking member 400 within the locking member through apertures 208 in either clockwise or counterclockwise direction, the cell chamber insert 300 can be easily locked and sealed within, or unlocked from, the chamber holder 200.

The holder 200 and the locking member(s) 400 are composed of any of a number of materials known to those skilled in the art that are appropriate for the intended use. In more particular embodiments, the materials composing the holder 200 and the locking member 400 are capable of being sterilized using any one or more of a number of techniques known to those skilled in the art, including but not limited to sterilization by chemical, gas, radiation or heat, for example, steam, more specifically a steam autoclave. More specifically such materials preferably are inert materials that do not corrode and include but are not limited to, stainless steel, aluminum, chrome and the like.

The chamber insert 300 includes a body member 302, a plurality of gaskets 304 and a plurality of cover glass elements, a top cover glass element 306a and a lower cover glass element 306b. The body member 302 includes a centrally located and axially extending through aperture 303 that in combination with the cover glass elements 306a,b defines and forms a central area 305 for the media, culture or cells that is served by the ports 308a–c that control the volume and flow of media as hereinafter described.

The body member 302 is composed of any of a number of materials known in the art that are appropriate for the intended use and which can be sterilized using any one or more of the sterilization techniques described herein. In a particular exemplary embodiment, the body member 302 is comprised of chlorotrifluoroethylene polymer, marketed as "KEL-F" by 3M Corporation. Other examples of the fluorocarbon polymers that are contemplated for use in the body member 302 of the present invention include polytetrafluoroethylene, marketed as "TEFLON" by DuPont, polytetrafluoroethylene containing perfluoroalkoxy side chains, and marketed as "PFA" by DuPont, ethylene tetrafluoroethylene copolymer (ETFE), marketed as "Tefzel" by DuPont, polyvinylidene fluoride, marketed as "Kynar" by Pennwalt Corporation. Additional examples of suitable fluorocarbon polymers that are contemplated for use in the body member 302 include fluorinated ethylene propylene polymer (FEP) marketed by DuPont.

At each end of the body member 302 one of the plurality of gaskets 304 is located so as to form a pressure boundary or seal between the body member and one of the cover glass elements 306a,b. In more particular embodiments, a shallow bore (e.g., "c" bore) is made at each end of the body member 302 to receive one of the plurality of gaskets 304 and one of the cover glass elements 306a,b as more clearly illustrated in FIG. 11. In this way, when the chamber insert 300 is assembled, the cover glass elements 306a,b in combination with the gaskets 304 seal the ends of the axial through aperture 303 so as to form or define the central area 305 yet allow for transmission of light. In exemplary embodiments, the volume of the central area 305 is preferably between about 1 cm$^3$ to about 4 cm$^3$, more preferably about 1 cm$^3$, more specifically about 2 cm$^3$, and yet still more particularly about 2.8 cm$^3$.

The cover glass elements 306a,b are made from any material known to those skilled in that allows for high resolution of the specimen of interest. Such materials include, but not are mot limited to, glass, quartz, and any other materials known to those skilled in the art that are translucent and impermeable to the gas(es) located within the central area 305. The gasket 304 is made from any number of materials known to those skilled in the art that is appropriate for the intended use. Such gasket materials include, but are not limited to polytetrafluoroethylene ("TEFLON").

Also, and as further described hereinafter, the lower cover glass element 306b is used to provide a surface for the culturing of the specimen of interest. For example, stem cells are plated on the lower cover glass element 306b, which can be, for example, a 24.5 mm cover slip. The lower glass element 306b further includes any material suitable for the attachment and growth of the desired cells, for example, a cover glass element as herein described that is covered with poly-ornithine or extracellular matrix components. Other suitable materials contemplated for use in the present invention for the growth of the cells of interest can include protein coated membranes, where the protein may be collagen, fibronectin, hemonectin, RGDS peptide, mixed bone marrow matrix protein, or the like. Various membrane materials as are known in the art are contemplated for use with the present invention and such materials include, but are not limited to polypropylene, polyethylene, polycarbonate, and polysulfonate.

The body member 302 also is configured so as to include a plurality of ports, two inlet ports 308a,b and an outlet port 308c, that generally extend radially between the central area 305 to the outer surface of the body member 302. A respective one of the tubular members or tubing members 320a–c of the chamber insert 300 is inserted into and secured within the through aperture that comprises each of the chamber insert inlet and outlet ports 308a–c. In this way, a portion of the tubing member, including one end of the tubing member, extends outwardly from the chamber insert 300 and so that another portion thereof, including another end of the tubing member, extends inwardly within the chamber body member 302 whereby said another end is fluidly coupled to the central area 305 of the chamber insert. In particular embodiments, the portion of the tubing members 320a–c extending within the chamber body member 302 is configured and sized so as to form a tight-fit, more specifically a press-fit, between the tubing member and the respective one of the inlet and outlet ports 308a–c.

Figure 12:
FIG. 12 is a cross-sectional view of the chamber insert tubing.

In more particular embodiments, and with reference to FIG. 12, each of the insert tubing members 320a–c is configured so as to include a first portion 324, a second portion 326 and a coupling member 322. The second portion 326 is configured and sized so as to form a tight-fit, more specifically a press-fit, between the second portion and the respective one of the inlet and outlet ports 308a–c. The coupling member 322 is any of a number of members or devices known to those skilled in the art, such as for example, a female/male Leur connection/coupler that can fluidly couple and interconnect tubular members or tubing. The coupling member 322 is interconnected and fluidly coupled to one end of the second portion 326 using any of a number of techniques known to those skilled in the art, including techniques such as brazing, swaging, soldering and the use of adhesives.

One end of the first portion 324 is fluidly coupled and interconnected to the other end of the second portion 326 and the other end of the first portion is fluidly coupled to a respective one of the inlet or outlet ports 308a–c and thereby coupled to the chamber insert central area 305. In an illustrative exemplary embodiment, the second portion 326 is stainless steel capillary tubing and the first portion 324 is 20-gauge stainless steel hypo tubing that is soldered inside the capillary tubing comprising the second portion.

Figure 13A:
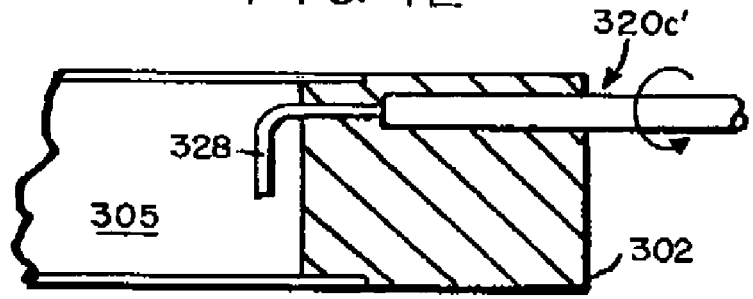
FIG. 13A is a partial cross-sectional view of an alternative embodiment for the chamber insert.
Figure 13B:
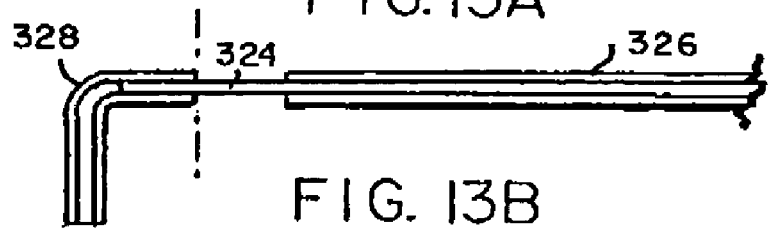
FIG. 13B is a cross-sectional view of the chamber insert tubing according to the alternative embodiment.

In an alternative embodiment and with reference to FIGS. 13A,B, the insert tubing member, the outlet tubing member 320c, that extends from the outlet port 308c is further configured and arranged with a third portion 328, so the outlet tubing member regulates or controls the volume of material (e.g., liquid material) within the central area 305 of the chamber insert 300 independent of the position of the outlet port 308c within the body member 302. In particular embodiments, such regulation or control is accomplished by selectively varying the length of the third portion 328 and/or by selectively rotating the tube assembly made up of the first through third portions 324–328 with respect to the outlet port 308c. In addition, a length of the first portion 324 is set so an end thereof extends with the central area 305. In this way, the height of the inlet of this tube assembly above the lower cover glass element 306b can be varied or adjusted to suit a particular application without requiring the location of the outlet port 308c to be adjusted for the particular application.

In more particular embodiments, the third portion 328 is tubular member that is secured to the end of the first portion 324 that extends into the central area 305 of the chamber insert 300. In more specific embodiments, the third portion 328 is secured to this end after the first and second portions 324, 326 have been inserted into the outlet aperture 308c. The third portion 328 is made of any of a number of materials known to those skilled in the art that is appropriate for the intended use, including but not limited to stainless steel and plastics such as polyethylene. In a particularly illustrative exemplary embodiment, the third portion comprises a length of polyethylene tubing that is slide over the end of the first portion 324 that extends into the central area 305, where the first portion 324 comprises 20-gauge stainless steel hypo tubing.

The inlet and outlet ports 308a–c also are arranged in the insert body member 302 such that they are aligned with the plurality of holder sidewall slots 210a–c, when the chamber insert 300 is disposed within the holder recess 202. In this way, each of the tubing members 320a–c of the chamber insert 300 pass through a respective one of the plurality of holder sidewall slots 210a–c and is fluidly coupled to a respective one of the plurality of interconnecting tubing 30a–c by the coupling member 322. Also, each of the sidewall slots 210a–c are preferably configured and sized such that the insert tubing members 320a–c passes along the length of the respective slot as the chamber insert 300 is being inserted or lowered into the holder recess 202.

In particular embodiments, the body member 302 is configured with a plurality of radial slots 310 and so that each of the inlet and the outlet ports 308a–c join a respective one of a plurality of radial slots 310 to control the volume and flow of media exiting the port connected thereto. In particular embodiments, the radial slots 310 and configured so as to distribute the media in a controlled, laminar flow. The radial slots 310 are arranged so one end of a radial slot is fluidly coupled to the one of the inlet or outlet ports 308a–c and the other end of which is fluidly coupled to the central area 305. In a particular embodiment, each of the radial slots 310 is preferably dimensioned so that the flow rate of media is about 0.2 ml/hour.

In more particular embodiments, the radial slots 310 are dimensioned so that they are between about 0.05 inches to about 0.25 inches wide, more particularly between about 0.075 to about 0.02 inches wide, and more specifically between about 0.01 inches to about 0.015 inches wide. Also, the depth of each radial slot 310 is established so as to be between about 0.03 inches to about 0.1 inches, more particularly between about 0.05 inches to about 0.08 inches, and more specifically between about 0.060 inches to about 0.065 inches. In addition, the length of each radial slot 310 is typically about 0.25 inches.

In particular illustrative embodiments, the volume of media within the chamber insert central area 305 during the culturing of the cells is between about 0.5 ml to about 2.5 ml. More particularly the volume of medium is about 2 ml, more specifically about 1.5 ml, still yet more particularly about 1.2 ml. Also, the rate of flow of medium into the central area 305 is between about 0.01 ml/hour to about 0.5 ml/hour, more particularly, about 0.01 ml/hour, more specifically about 0.1 ml/hour, and still yet more particularly about 0.2 ml/hour.

In further embodiments, the body member 302 is configured so as to include a side port 330 that is formed within the body member at an angle with respect to a horizontal plane or a normal to a surface of the body member in which the side port (e.g., an angled through aperture) is located and the stem cell chamber 100 further includes a ball joint assembly 340 that is disposed with the side port. The body member 302 also is configured such that the side port 330 is aligned with the slotted through aperture 212 in the chamber holder 200, when the chamber insert 300 is disposed within the holder recess 202. In an exemplary illustrative embodiment the side port 340 is at an angle of about 16 degrees with respect to the horizontal plane and the holder slotted through aperture 212 also is arranged so as to be at a corresponding angle.

The ball joint assembly 340 includes a ball 342, a ring seal 344 and a sleeve 346. The ball 342 is configured so as to include a through aperture therein 348 in which is received a close-fitting capillary electrode 350 or tubular member, preferably made of glass, borosilicate and the like. Such a through aperture 348 can be formed in the ball 342 for example by a reamer. The capillary electrode 350 is arranged so that one end thereof opens into the central area 305, more particularly the culture area that contains the specimen of interest. The capillary electrode 350 provides a mechanism to allow delivery of molecules such as chemokines, growth factors and the like or the measurement of ions, anions, cations, electric impulses and the like.

When the chamber insert 300 is inserted into the holder recess 202, the capillary electrode 350 also extends outwardly from the holder slotted through aperture 212 and is moveably vertically with the circular portion or the slot of the slotted through aperture and radially within the circular portion. In an exemplary illustrative embodiment, the capillary electrode is connected to a micromanipulator that is external to the stem cell chamber 100.

Figure 17:
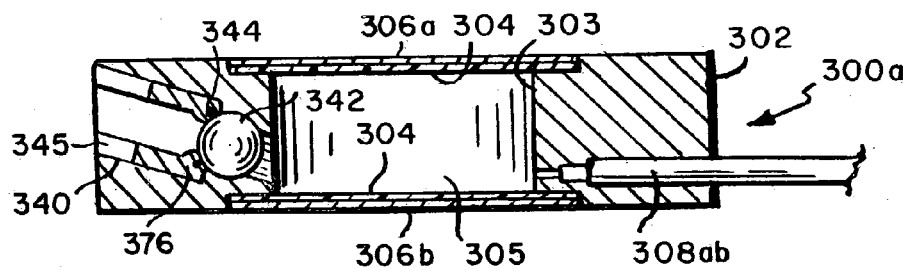
FIG. 17 is a cross-sectional view of the chamber insert taken along line 17—17 of FIG. 15.

Although the through aperture 348 in the ball 342 is described in connection with use of an capillary electrode 350, this shall not be construed as limiting the ball to a specific use. The ball 342 can be configured so as to have any of a number of differently sized through aperture, whose size is established for use in a particular technique and/or instrumentality to be passed there through. It also is contemplated that balls with differently sized through apertures can be interchanged with one another. In further embodiments, the ball 342 can be configured without a through aperture (i.e., a solid ball) as illustrated in FIG. 17, a member or plug can be inserted into the through aperture 348 to seal the ball 342, or the ball can be manipulated so the through aperture is not in fluid communication with the central area 305.

The ball 342 is suitably comprised of any of a number of materials known in the art that are appropriate for the intended use, more particularly, the ball is comprised of any of a number of different kinds of plastics or hard rubber such as for example, Delrin, Teflon, Viton and the like. In exemplary illustrative embodiments, the ball 342 is configured so as to have a diameter between about 0.1 inches to about 0.2 inches, more particularly a diameter of about 0.18 inches (3/16 of an inch).

As indicated above, the ball joint assembly 340 also includes a ring seal 344 that in an illustrative exemplary embodiment comprises an O-ring type of ring seal made from any of a number of materials known to those skilled in the art such as silicone rubber or like materials. In the illustrative embodiment, the O-ring type of compression ring 344 fits against the ball 342 so as to apply a sealing force between the ball and the chamber insert body member 302. The fit produced preferably is an air tight fit but also one that provides a sealing force between the ball 342 and the body member 302 as well as allowing freedom of rotation of the ball joint.

The sleeve 346 is configured so as to include a through passage 345 that extend axially along the length of the sleeve. The sleeve through passage 345 is dimensioned and configured such that the capillary electrode 350 extending outwardly from the ball 342 is received and passed through the sleeve through passage 345. In addition, the sleeve through passage 345 is dimensioned so the capillary electrode 350 is moveable therein. The sleeve 346 is made from any of a number of non-corrosive materials including, for example, stainless steel that are appropriate for the intended use and so as to be capable of being sterilized using any of the sterilization techniques described herein. In illustrative exemplary embodiments, the sleeve 346 is cylindrical in shape with a diameter of about 0.25 inches and the through aperture 345 has a diameter of about 0.14 inches. The overall length of the sleeve is between about 0.09 inches to about 0.2 inches, more particularly, about 0.125 inches.

The ball joint assembly 340 is held together, and in place within the chamber insert body member 302, using any of a number of techniques known to those skilled in the art. In an illustrative exemplary embodiment, the mechanism for holding the ball joint assembly 340 together and within the body member 302 is a setscrew 341. In the illustrated embodiment, the setscrew 341 is inserted into a threaded through aperture 332 such that it mechanically engages the sleeve 346, thereby fixedly securing the sleeve.

If it is desired to electrically monitor the growth and/or proliferation processes for example, the capillary electrode 350 is arranged so it can be used to determine whether electrophysiologically active cells are in fact non-neuronal, and that glial cells do contain voltage-sensitive Na channels that evoke action potential-like conductances. Also, the capillary electrode 350 can be filled with medium comprising, for example, growth factors or recording medium and placed through the ball 342 into the central area 305 (see illustrative example of chamber described below).

The use of the stem cell chamber 100 of the present invention can be best understood from the following discussion and with reference to FIGS. 1–13. Reference also should be made to the foregoing discussion relating to these figures for details and elements not otherwise described in detail in the following. The stem cell chamber 100 is assembled partially so that the chamber insert 300 is located with the holder recess 202 with the upper cover glass element 306b off so as to expose the central area 305 of the central chamber 300. The cells to be cultured are disposed within the central area 305 using any of a number of techniques known to those skilled in the art and the central area is filled completely with a medium that is equilibrated for the right gas environment in an incubator.

The stem cell chamber 100 is completely assembled so the chamber insert 300 is locked and sealed within the holder 200. As hereinabove described such locking and sealing is accomplished by rotating each of the locking members 400 within the locking member through apertures 208 so a force is applied to the plate member 500 and thus a sealing force also is applied to each of the upper and lower glass elements 306a,b. The assembled and sealed stem cell chamber 100 is then positioned within the environmental chamber 20 and is preferably disposed upon or placed over the microscope stage 50. Each of the insert tubing members 320a,b fluidly coupled to each of and is appropriately connected to the interconnecting tubing 30a,b that are in turn interconnected to an external gas source and a medium source, for example via a syringe pump.

If the cell culturing process involves the use of the capillary electrode 350, the capillary electrode is inserted into the through aperture 348 in the ball 342 so one end thereof extends into the central area 305. The capillary electrode 350 also is connected via a flexible tube and interposed holder element to an axoclamp headstage that is held by a micromanipulator.

After, the stem cell chamber 100 is appropriately interconnected to the interconnecting tubing 30a–c and placed over the microscope stage 50, the assembly is contained within environmental chamber 20. Thereafter controls are activated so that the environment within the environmental chamber (e.g., atmospheric temperature) is appropriately controlled and regulated so as to establish environmental conditions that are conducive to cell growth and to the viewing of the cells within the central area 305 of the chamber insert 300 using the microscope stage. As also indicated above, the environmental chamber 20 also is preferably sealed so as to establish light tight conditions within the environmental chamber.

In illustrative exemplary embodiments, the external gas source is a sealed circulating system that maintains the desired atmospheric culture conditions within the central area 305, such as for example an atmosphere including 5% carbon dioxide, 5% oxygen. Also, the medium source is a syringe pump that is adjusted so the medium flows from the syringe pump to the central area 305 at a desired rate. The syringe pump is in turn connected to a source of the medium as is known to those skilled in the art.

In more particular embodiments, one of the insert tubing members, a first inlet tubing member 320a, is interconnected to the gas source so gas is admitted to the central area 305 and so bubbles are not generally formed in the medium within the central area as the gas is being introduced therein. Similarly, another of the insert tubing members, a second inlet tubing member 320b, is interconnected to the medium source, such as the syringe pump. Correspondingly, the outlet tubing member 320c is interconnected to the outlet port 308c and in turn is appropriately connected to a repository for the medium/gas being outputted from the central area 305. After appropriately interconnecting the inlet and outlet tubing members 320a–c, some of the media is removed from the central area 305, for example about 1.5 ml, and is replaced by a cover gas or gas atmosphere that is constituted so as to be appropriate for the culturing of the cells and the medium being used, such as for example a gas being constituted so has to have a concentration of 5% $CO_2$ 5% $O_2$.

Thereafter, and as when desired the user can observe the cells being cultured via the microscope stage 50. The user continues the flow of medium into, and correspondingly out of, the central area 305 until it is determined that the culturing process should be terminated. In addition, the user also can continue the flow of the gas mixture into the central area 305 until it is determined that such flow should be terminated. Other operations as herein described such as those involving the capillary electrode 350 also are performed as when desired by the user.

For example, the user can configure the cell culture system 10 of the present invention so as to be capable of monitoring the dynamic processes that occur during proliferation and differentiation of stem cells such as central nervous system (CNS) stem cells/embryonic stem cells. In particular, the cell culture system 10 is configured and arranged so as to allow monitoring of these dynamic processes continually. In addtion, the cell culture system can be configured so as to focally manipulate the cells by focal application of growth factors such as BMP, CNTF and other growth factors. Further, the cell system can be configured and arranged so as to be capable of electrical recording from the cells. As indicated herein, such a cell culture s system is particularly suited for the long term culture of cells, particularly CNS stem cells, embryonic stem cells and the like.

It should be recognized that the cell culture system 10 of the present invention also can be suitably used in conjunction with any type of a wide variety of analysis equipment, materials or reagents, including equipment, materials and reagents used with standard microscope slides, such as for example, coverslips, slide washers, pipettors, or robotic systems as is known to those skilled in the art. Additionally, the cell culture system 10 of the present invention is adaptable for use with any type of instrument or device capable of analyzing or reading a standard microscope slide including for example, microscopes, scanners, readers, imagers or the like.

After a given cell culturing process is determined to be completed, the user disconnects the stem cell chamber 100 from the interconnecting tubing 30a–c, removes it from the environmental chamber 20 and disassembles the stem cell chamber. The re-useable components of the stem cell chamber 100 such as the chamber holder 200 and the chamber insert 300 are appropriately cleaned and sterilized for further use.

In a preferred embodiment, a coverslip or other analysis substrate can be treated to provide differentiated areas that inhibit or prevent cell migration during culturing. In a preferred aspect, material (e.g., a releasable tape) that has openings is applied to a coverslip. The openings provide segregated areas where cells can be cultured without migration to other areas even over extended periods such as 1 to 10 days or more. Suitable materials include commercially available tapes such as Kapton (polyimide tape with small openings available from Robert McKeown, N.J.).

The long term culturing of cells using the cell culture system 10 and device of the present invention is useful in identifying, for example, CNS stem cells, defining conditions that stably maintain CNS stem cell properties for long-term, and controlling their differentiation into mature cell types. Different procedures can be used for isolating, propagating, and differentiating the CNS stem cells. For example, the initial dissociation of cells from tissue performed by mechanical trituration or by enzymatic digestion. With adult tissue, it is necessary to first enzymatically digest the tissue and then dissociate the cells from the tissue by mechanical trituration.

As used herein, "trituration" means gentle agitation of cell aggregates caused by fluid movement occurring during repetitive pipetting action by which individual cells become loose and dissociated from neighboring cells. Trituration is conducted in a saline solution free of divalent cations whose absence aids break-up of interactions among cell-adhesion proteins on cell surface. Rapidly dividing stem cells in the ventricular zone are only weakly adherent and simply removing the divalent cations from the medium and gentle agitation by pipetting are sufficient to dissociate the tissue into mostly single cells.

The cells are then cultured, preferably, in the complete absence of serum. Even a brief exposure to serum deleteriously affects the differentiation capacity of the stem cells so that they are no longer able to differentiate into neurons and oligodendrocytes. If required, precoating the lower cover glass element 306b with poly-L-omithine and fibronectin facilitates the adhesion of the cells to the plates. Manipulation of the cells using the ball-joint assembly 340 can be carried out by addition of growth factors, such as for example, basic fibroblast growth factor (bFGF), EGF, TGF-alpha, or acidic FGF (aFGF). Differentiation of the CNS stem cells is achieved by simply removing the mitogen, bFGF or other selected growth factor, from the medium. Specification of the cell types, i.e., neurons, oligodendrocytes, and astrocytes, occurs constitutively.

In a preferred embodiment, the cell culture system 10 and device of the present invention is utilized to obtain a homogeneous population of the CNS stem cells that can be differentiated into neurons, oligodendrocytes, and astrocytes with control and efficiency; production of a large number of the CNS stem cells with the potential to form many different neuronal subtypes, oligodendrocytes, and astrocytes that can be transplanted into a brain; controlled differentiation in vitro under serum-free conditions which allows the search for novel growth factors and cytokines; rapidly dividing cells accessible to genetic manipulation for introduction of foreign genes; generation of mature neurons in vitro suitable for genetic and pharmacological screening; and, direct derivation of intermediate precursor cells from the stem cells for enrichment of a single population of cells.

The long term culture permitted by the cell culture system 10 and device of the present invention also is useful for directed differentiation of the cells by treating them with specific growth factors. One practical significance of this directed differentiation to biotechnology is that a single cell type can be enriched in vitro. Thus, a novel application of previously discovered growth factors, for example, $PDGF_{37}$ (platelet-derived growth factor), CNTF (ciliary neurotrophic factor), and T3 (thyroid hormone, tri-iodothyronine) would be to direct the CNS stem cells to generate neurons, astrocytes, and oligodendrocytes, respectively. Another practical significance, especially for PDGF, is that PDGF-induced neurons appear to be actually neuronal progenitors that can further proliferate and expand in culture by PDGF. These cells differentiate only to neurons or to neurons and oligodendrocytes and differ from the stem cells. Isolation of neuronal progenitors from mammalian CNS by PDGF has not been described previously.

Any cell can be used in the method, cell culture system 10 or device of the present invention, including but not limited to, stem cells, CNS stem cells, embryonic stem cells, thymocytes, precursor cells and the like. A precursor cell population includes cells of a mesodermal derived cellular lineage, more particularly of hematopoietic lineage, endothelial lineage, muscle cell lineage, epithelial cell lineage and neural cell lineage. Depending on the desired cells, different growth factors which may be included in the growth medium, either by stromal cell secretion or addition, are GM-CSF, G-CSF, or M-CSF, interleukins 1–7, particularly 1, 3, 6, and 7, TGFα or TGFβ, erythropoietin, or the like, particularly human factors. For example, addition of about 0.5–2 ng/ml, preferably about 1 ng/ml G-MCSF, and about 0.5–2 ng/ml, preferably 1 ng/ml, as well as a 0.1–2 U/ml/day of final concentration of erythropoietin, from about 100–300 ng/ml/day of G-CSF and about 1–10 ng/ml/day of stem cell growth factor (S-CSF, also referenced as Mast Cell Growth Factor or Kit ligand). It is to be understood that the amount of each growth factor to be used is determined empirically and will vary depending on the purity and method of production of the factors. Generally, concentrations between 0.5 and 100 ng/ml are sufficient, more often between 0.5 and 50 ng/ml. Where more than one growth factor is used, the optimum amount of each factor should preferably be determined in combination with the other factors to be used. This is because some growth factors can modulate the activity of other growth factors, necessitating that they be used sequentially rather than simultaneously, while in other instances, growth factors may act synergistically. Still other growth factors may enhance proliferation or differentiation along one pathway, while suppressing another pathway of interest.

A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e., cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells.

Also as used herein, the term "pluripotent cell" refers to a cell capable of developing into a variety (albeit not all) lineages and are at least able to develop into all hematopoietic lineages (e.g., lymphoid, erythroid, and thrombocytic lineages). For example, a pluripotent cell can differ from a totipotent cell by having the ability to develop into all cell lineages except endothelial cells. A "pluripotent population of cells" refers to a composition of cells capable of developing into less than all lineages of cells but at least into all hematopoietic lineages. As such, a totipotent cell or composition of cells is less developed than a pluripotent cell or compositions of cells. As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

A stem cell population of the present invention is capable of developing into cells of mesodermal cell lineage, of ectodermal cell lineage or of endodermal cell lineage. As used herein, mesodermal cells include cells of connective tissue, bone, cartilage, muscle, blood and blood vessel, lymphatic and lymphoid organ, notochord, pleura, pericardium, peritoneum, kidney and gonad. Ectodermal cells include epidermal tissue cells, such as those of nail, hair, glands of the skin, the nervous system, the external sense organs (e.g., eyes and ears) and mucous membranes (such as those of the mouth and anus). Endodermal cells include cells of the epithelium such as those of the pharynx, respiratory tract (except the nose), digestive tract, bladder and urethra cells. Preferred cells within a stem cell population of the present invention include cells of at least one of the following cellular lineages: hematopoietic cell lineage, endothelial cell lineage, epithelial cell lineage, muscle cell lineage and neural cell lineage. Other preferred cells within a stem cell population of the present invention include cells of erythroid lineage, endothelial lineage, leukocyte lineage, thrombocyte lineage, erythroid lineage (including primitive and definitive erythroid lineages), macrophage lineage, neutrophil lineage, mast cell lineage, megakaryocyte lineage, natural killer cell lineage, eosinophil lineage, T cell lineage, endothelial cell lineage and B cell lineage.

Various techniques may be employed to separate the cells by initially removing cells of dedicated lineage. Monoclonal antibodies are particularly useful for identifying markers associated with particular cell lineages and/or stages of differentiation.

If desired, a large proportion of terminally differentiated cells may be removed by initially using a "relatively crude" separation. For example, magnetic bead separations can be used initially to remove large numbers of lineage committed cells. Desirably, at least about 80%, usually at least 70% of the total hematopoietic cells will be removed.

Procedures for separation include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique. Techniques providing accurate separation include but are not limited to, flow cytometry, which can have varying degrees of sophistication, e.g., a plurality of color channels, low angle and obtuse light scattering detecting channels, impedance channels, etc.

The cell culture system 10 and device of the present invention described herein, also is highly useful for generation of desired cells that are used for treatment of various diseases. There is significant interest in the ability to use cells for a wide variety of therapeutic purposes. The hematopoietic system exemplifies the extraordinary range of cells involved in protection of mammalian hosts from pathogens, toxins, neoplastic cells, and other diseases. The hematopoietic system is believed to evolve from a single stem cell, from which all the lineages of the hematopoietic system derive. The particular manner in which the stem cell proliferates and differentiates to become determined in its lineage is not completely understood, nor are the factors defined. However, once the stem cell has become dedicated to a particular lineage, there appear to be a number of factors, for example colony stimulating factors, which allow, and may direct the stem cell to a particular mature cell lineage.

There are many uses for blood cells. Platelets find use in protection against hemorrhaging, as well as a source of platelet derived growth factor. Red blood cells can find use in transfusions to support the transport of oxygen. Specific lymphocytes may find application in the treatment of various diseases, where the lymphocyte is specifically sensitized to an epitope of an antigen.

Stem cells may be used for genetic therapy as well as for rescue from high dose cancer chemotherapy. These and many other purposes are contemplated for use with the system, devices and methodology of the present invention.

Figure 14:
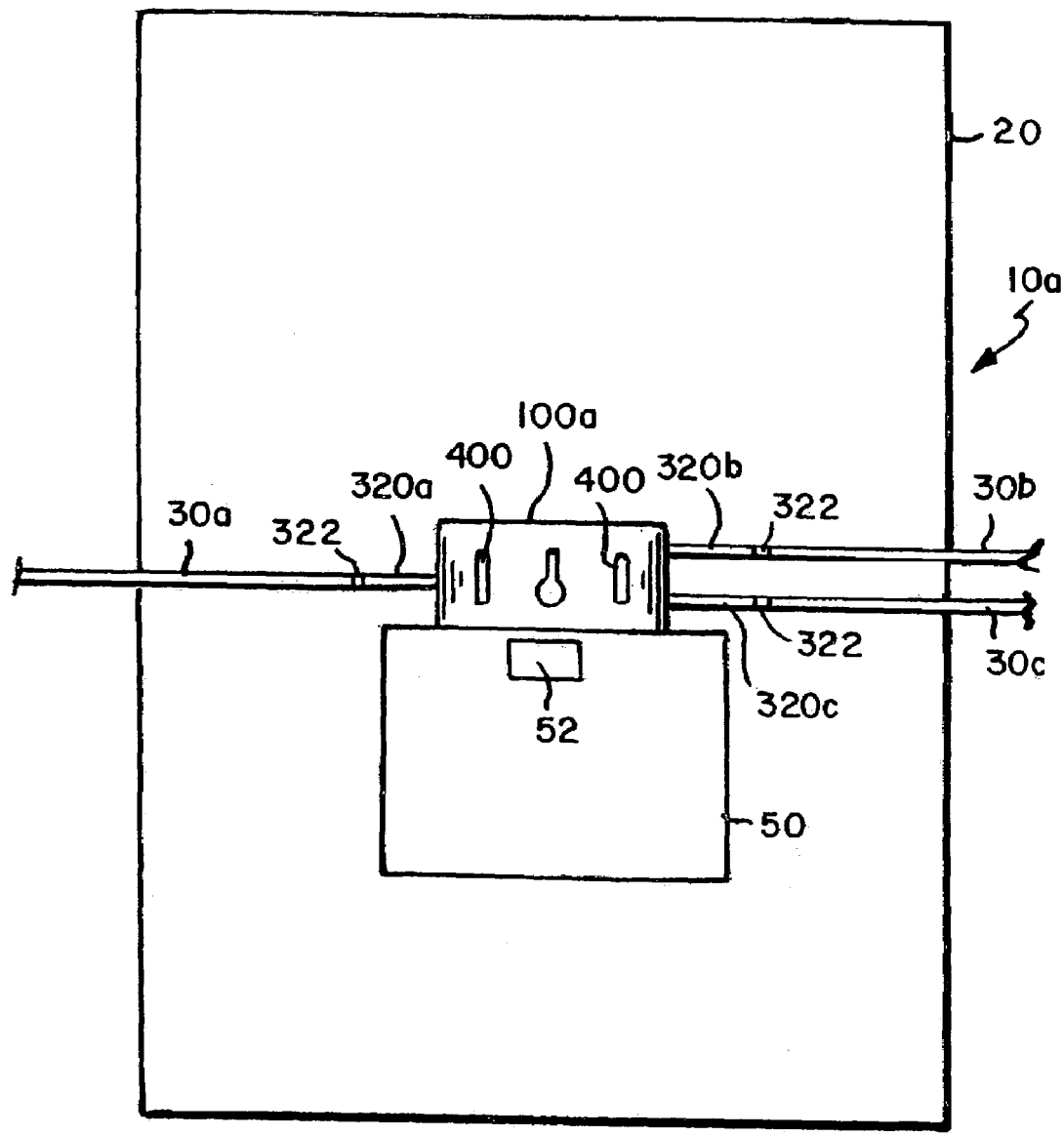
FIG. 14 is a schematic block diagram illustrating a cell culturing system according to another aspect of the present invention.
Figures 15, 16:
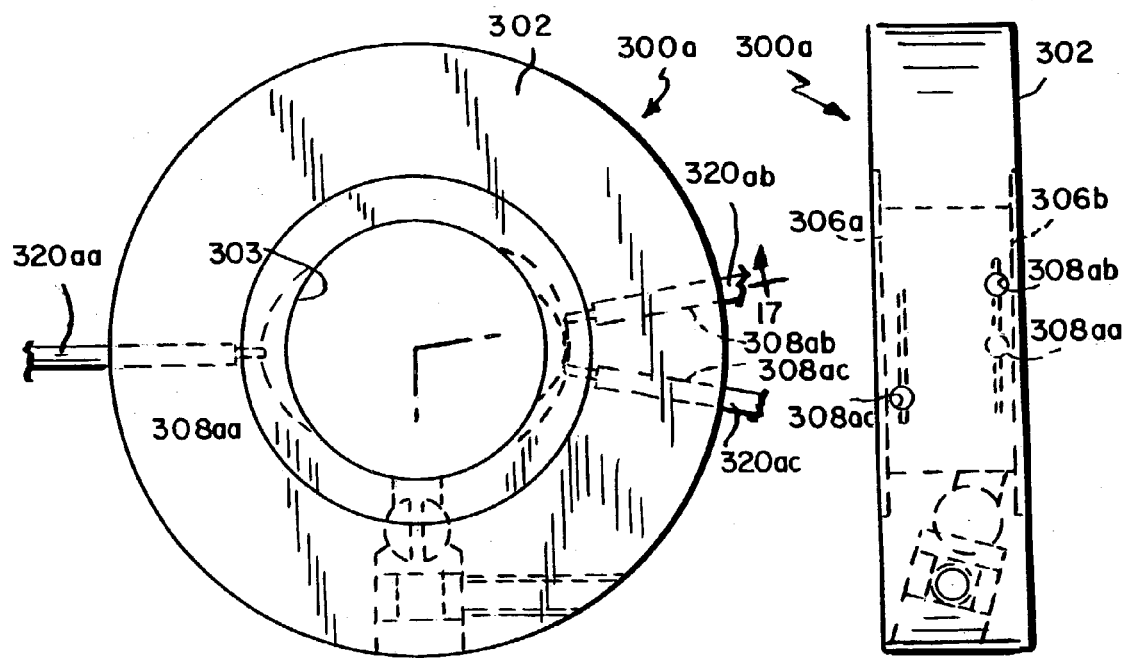
FIG. 15 is a top view of a chamber insert for the stem cell chamber of FIG. 14.
FIG. 16 is a side view of the chamber insert of FIG. 15 without the chamber insert tubing members for clarity.
Figure 18:
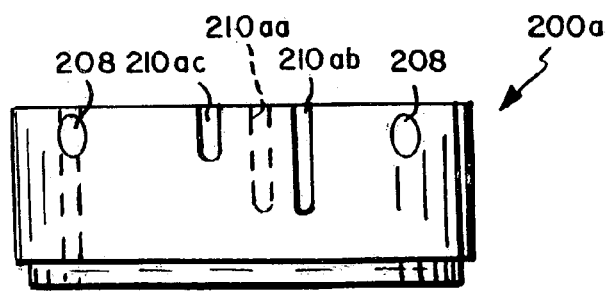
FIG. 18 is a side view of the stem cell chamber holder for the stem cell chamber of FIG. 14.

Referring now to FIG. 14 therein is shown a schematic block diagram of a culturing system 10a according to another aspect of the present invention that is used for the long term growth and monitoring of cells. Reference also should be made to FIGS. 15–17 for further details of the chamber insert 300a and FIG. 18 for further details of the chamber holder 100a according to this aspect of the present invention. In addition, reference shall be made to FIGS. 1–13 and the foregoing discussion regarding FIGS. 1–13 for those features, elements or components denoted by a common reference numeral and reference also shall be made to these figures and the foregoing discussion for features, elements or components relating to those features, elements or components described hereinafter where noted in the following. Such a culturing system 10a according to this aspect of the present invention includes an environmental chamber 20, a microscope stage 50 a stem cell chamber 100a and the interconnecting tubing 30a–c that is fluidly interconnected to the stem cell chamber 100.

The stem cell chamber 100a according to this aspect of the present invention differs from that described hereinabove in regards to FIGS. 1–13, in a number of respects. The plurality of ports in the chamber insert 300a that comprise the inlet and outlet ports for the chamber insert are configured and arranged differently, the sidewall through slots in the chamber holder are configured and arranged differently, and this aspect of the present invention illustrates the case in which the ball 342 of the ball joint assembly 340 is solid in construction. Also, the use of the stem cell chamber 100a in regards to the introducing and maintaining a particular gas concentration in the central area 305 thereof differs from that described herein above in connection with FIGS. 1–13.

According to this aspect of the present invention, the chamber insert 300a includes an the outlet port 308aa and two inlet ports 308ab, 308ac to which is fluidly coupled and interconnected respectively, the outlet tubing member 320aa and the inlet tubing members 320ab, 320ac. In more particular embodiments, one of the inlet ports 308ac is fluidly coupled to the gas source and the other of the inlet ports 308ab is fluidly coupled to the medium source. As to the construction, sizing and configuration of each of the plurality of ports 308aa–cc, their fluid interconnection to the radial slots 340 and the construction, sizing and configuration of each of the tubing members 320aa–cc, reference shall be made to the foregoing description for the inlet and outlet tubing members 320a–c, insert ports 308a–c and the interconnection of the ports 308a–c to the radial slots 340 provided herein above in the discussion of FIGS. 1–13.

The outlet port 308aa is arranged in the chamber insert 300a so as to be in a different plane from that of the inlet port 308ac for the gas and so as to be in the same general plane as the inlet port 308ab for the fluid medium. As such, the sidewall slots 210aa–ac in the chamber holder 200a are arranged so as to complement this arrangement of the inlet ports 308aa–ac. As to the construction, sizing and configuration of each of the sidewall slots 210aa–ac in the chamber holder 200a, reference shall be made to the foregoing description for the sidewall slots 210a–c provided herein above in the discussion of FIGS. 1–13.

Reference also should be made to the foregoing discussion regarding use of the stem cell chamber 100 as described in connection with FIGS. 1–13, which also apply to the use of the stem cell chamber 100a according to said another aspect of the present invention with the following modification. After filing the central area 305 with the medium a gas is introduced or admitted while some of the medium is drawn off. After competing this process, so the desired atmospheric environmental conditions is established within the central area 305, the process of admitting gas is ended or stopped. In more particular embodiments, after ending the admission of the gas, the interconnecting tubing 30c from the gas source is decoupled from the corresponding inlet tubing member 320ac and this inlet tubing member 320ac is sealed of, for example, a plug or equivalent device or member is connected to the inlet tubing member 320ac sealing the tubing member.

The following non-limiting examples are illustrative of the invention.

EXAMPLE 1

Long Term Cell Culture of Stem Cells

To better understand the dynamic processes that occur during proliferation and differentiation of CNS stem cells/embryonic stem cells (Stem cell differentiation and synapse formation take 10 days), a culturing system is established that allows users to monitor these events continually and also to allow a user to focally manipulate the cells by focal application of growth factors such as BMP, CNTF and other growth factors. Such a system also allows the electrical recording from the cells. In order to grow the cells for long period of time on a microscope stage there is provided an environmental chamber 20 and a cell chamber 100 in which is disposed the cells to be cultured, which cell chamber comprises another form of an environmental chamber. The environmental chamber 20 surrounds the microscope stage 50 and is used to warm the culture and the microscope stage to about 37° C. By keeping the microscope stage 50 continually in the same temperature as the culture, the microscope stage 50 is prevented from becoming a heat sink and this also prevents drift in focus. The cell chamber 100 is a mini gas tight chamber that is placed over the microscope stage 50, which cell chamber is connected to a sealed circulating system that maintain gases at 5% $CO_2$, 5% $O_2$. This culture system allows a user to grow cells over the microscope stage 50 while imaging them for long periods of time (e.g., 2 weeks).

The mini gas tight chamber comprising the cell chamber 100 is a wet-dry type of chamber having an interior volume of 2.835 ml, where about 1.2 ml is filed with medium and the rest is filled with the appropriate gas mixture which in this particular example, is 5% $CO_2$, 5% $O_2$ and 90% $N_2$. The stem cells are plated on 24.5 mm cover slip that comprises the lower cover glass element 306b, which also comprises the bottom of the interior volume defined within cell chamber. An electrode is pulled from borosilicate 1.5 mm capillary (e.g., Sutter Instrument) and the electrode is filled with medium with growth factor or recording medium and placed through the ball 342 of the ball joint assembly 340 in the interior volume (e.g., central area 305) within the cell chamber.

The interior volume or central area 305 of the cell chamber is initially filled completely with medium that was equilibrated for the right gas environment in an incubator. At this stage the cell chamber 100 is completely assembled and sealed and 1.6 ml of the volume is replaced by 5% $CO_2$ 5% $O_2$ cover gas/gas atmosphere. The cell chamber 100 is placed over the microscope stage 50 and it is being connected to sealed syringe pump through stainless steel tubes comprising the interconnecting tubing 30a–c and the syringe pump is adjusted so the rate of medium flow is 0.2 ml/hour. The electrode is connected through a 1 cm flexible tube to an axoclamp headstage that is held by a micromanipulator.

EXAMPLE 2

Long Term Cell Culture System

The stem cell chamber 100 is comprised of a holder 200 made of stainless steel, a chamber insert 300 made of KEL-F, a stainless steel pressure plate 506 with a silicone rubber disc 504 bonded to it and locking members 400 made of stainless steel.

The holder 200 is a receptacle for the chamber insert 300, the pressure plate 506 and locking members 400 and also allows quick and convenient exchange of the cover glass elements 306a,b and the specimen/cells. The bottom 206 in the holder 200 provides for close proximity of the specimen/cells to the microscope objective 52 for high resolution microscopy.

The chamber insert 300 has a central area 305 for the media and that is served by ports 308a–c that control the volume and flow of media. These ports 308a–c join radial slots 310 that distribute the media in a controlled, laminar flow. A shallow bore ("c" bore) is provided at each end of the chamber insert 300 for Teflon gasket 304 and cover glass element 306a,b. The cover glass elements 306a,b closes the central area 305 of the chamber insert 300, allows for transmission of light into the central area 305, and the lower cover glass element 306b provides a surface for the specimen of interest. A port 344 is machined in the side of the chamber insert 300, at an angle, which port receives therein a ball joint assembly 340, which includes a ball 342, a silicone rubber "O" ring seal 344 and a stainless steel cylinder that comprises the sleeve 346. The ball 342 is comprised of several different kinds of plastics or hard rubber such as for example, Delrin, Teflon, Viton and the like. A setscrew 341 holds the ball joint assembly 340 in place within the port 344. The ball 342 in the assembly 340 has a hole 348 for a close fitting glass tube, where the tube can be used to hold an electrode or can be used as a micropipette. Either version can be used to monitor or influence the specimen of interest. All components are suitable for sterilization by chemical, gas, radiation or steam autoclave.

All documents mentioned herein are incorporated herein by reference.

Although various embodiments, including a preferred embodiment of the present invention have been described using specific terms, the foregoing description of the invention is merely illustrative thereof, and it is understood that variations and modifications can be effected without departing from the spirit or scope of the invention as set forth in the following claims.

What is claimed is:

1. A cell culture system comprising:
   a microscopic viewing apparatus;
   a cell culture chamber including a holder having a recess, and an insert member received in the holder recess, the insert member having first and second inlet ports, a single outlet port, a side port and an interior volume in fluid communication with said first and second inlet ports and said single outlet port in which cells are cultured;
   a first inlet tubing member received in the first inlet port, the first inlet tubing member being connected to a gas source for controlling the flow of gas to the interior volume;
   a second inlet tubing member received in the second inlet port, the second inlet tubing member being connected to a medium source for controlling the flow ofuiedium to the interior volume;
   a single outlet tubing member received in the outlet port for removing gas and medium from the interior volume, wherein the insert member is constructed such that the gas and medium introduced into the interior volume only exit through said single outlet port; and
   an electrode disposed in the side port for manipulating the cells contained in the interior volume, the electrode having one end that is movable in the interior volume for manipulating the cells;
   wherein the cell culture chamber and the microscopic viewing apparatus are arranged such that the viewing apparatus can view cells being cultured in the chamber interior volume.

2. The cell culture system of claim 1 wherein the cell culture chamber is configured so as to allow light to pass through the chamber interior volume.

3. The cell culture system of claim 1, wherein the cell culture chamber comprises:
   a plurality of through apertures in communication with the interior volume that form the first and second inlet ports and the outlet port being used to control volume and flow of gas and medium in the chamber interior volume.

4. The cell culture system of claim 1, further comprising:
   a ball joint assembly attached to the insert member, the ball joint assembly holding the electrode or a tubular member.

5. The cell culture system of claim 1 wherein the cell culture chamber further comprises:
   a mechanism for securing the insert member within the holder recess.

6. The cell culture system of claim 1, wherein the insert member comprises:
   a body member having a through aperture extending along an axis thereof;
   a plurality of translucent members, a portion of each allowing light to pass therethrough;
   wherein one of the plurality of translucent members is positioned at one end of the body member through aperture so as to form a seal at said one end and another of the plurality of translucent members is positioned at another end of the body member through aperture so as to form a seal at said another end thereby defining the chamber interior volume.

7. The cell culture system of claim 6 wherein the cell culture chamber further comprises:
   a mechanism for securing the insert member and the plurality of translucent members within the holder recess.

8. The cell culture system of claim 1 wherein the cell culture chamber comprises stem cells.

9. The cell culture system of claim 8 wherein the stem cells are manipulated by the electrode to monitor their growth and/or proliferation.

10. A cell culture chamber comprising:
    a holder having a recess;
    an insert member received in the holder recess, the insert member having first and second inlet ports, a single outlet port, a side port and an interior volume in fluid communication with said first and second inlet ports and said single outlet port in which stern cells are cultured;

a first inlet tubing member received in the first inlet port, the first inlet tubing member being connected to a gas source for controlling the flow of gas to the interior volume;

a second inlet tubing member received in the second inlet port, the second inlet tubing member being connected to a medium source for controlling the flow of medium to the interior volume;

a single outlet tubing member reecived in the outlet port for removing gas and medium from the interior volume, wherein the insert member is constructed such that the gas and medium introduced into the interior volume only exit through said single outlet port; and an electrode disposed in the side port for manipulating the stem cells contained in the interior volume, the electrode having one end that is movable in the interior volume for manipulating the stem cells.

11. The cell culture chamber of claim 10, further comprising:

a plurality of through apertures in communication with the interior volume that form the first and second inlet ports and the outlet port being used to control volume and flow of gas and medium in the chamber interior volume.

12. The cell culture chamber of claim 10, further comprising:

a ball joint assembly attached to the insert member, the ball joint assembly holding the electrode or a tubular member.

13. The cell culture chamber of claim 10, further comprising:

a mechanism for securing the insert member within the holder recess.

14. The cell culture chamber of claim 10, wherein the insert member comprises:

a body member having a through aperture extending along an axis thereof;

a plurality of translucent members, a portion of each allowing light to pass therethrough;

wherein one ofthe plurality of translucent members is positioned at one end of the body member through aperture so as to form a seal at said one end and another of the plurality of translucent members is positioned at another end of the body member through aperture so as to form a seal at said another end thereby defining the chamber interior volume.

15. The cell culture chamber of claim 14 further comprising:

a mechanism for securing the insert member and the plurality of translucent members within the holder recess.

16. The cell culture system of claim 10 wherein the stem cells are manipulated by the electrode to monitor their growth and/or proliferation.

17. A cell culture system comprising:

a cell culture chamber including a holder having a recess, and an insert member received in the holder recess, the insert member having first and second inlet ports, a single outlet port, a side port and an interior volume in fluid communication with said first and second inlet ports and said single outlet port;

a first inlet tubing member received in the first inlet port, the first inlet tubing member being connected to a gas source for controlling the flow of gas to the interior volume;

a second inlet tubing member received in the second inlet port, the second inlet tubing member being connected to a medium source for controlling the flow of medium to the interior volume;

a single outlet tubing member received in the outlet port for removing gas and medium from the interior volume, wherein the insert member is constructed such that the gas and medium introduced into the interior volume only exit through said single outlet port;

stem cells loaded within the interior volume; and a ball joint assembly disposed in the side port, the ball joint assembly holding an electrode that is movable in the interior volume for manipulating the stem cells contained in the interior volume.

18. The cell culture system of claim 17 wherein the interior volume can be maintained under desired environmental conditions.

19. The cell culture system of claim 17 wherein the cell culture chamber and a microscopic viewing apparatus are arranged such that the viewing apparatus can view cells being cultured in the interior volume.

20. The cell culture system of claim 17, further comprising:

a plurality of through apertures in communication with the interior volume that form the first and second inlet ports and the outlet port being used to control volume and flow of gas and medium in the interior volume.

* * * * *